United States Patent
Wakevainen

[19]

[11] Patent Number: 5,813,597
[45] Date of Patent: Sep. 29, 1998

[54] DUAL ORIENTATION DISPENSER CARTON

[75] Inventor: Gary T. Wakevainen, Loveland, Ohio

[73] Assignee: Ethicon Endo-Surgery, Inc., Cincinnati, Ohio

[21] Appl. No.: 732,544

[22] Filed: Oct. 15, 1996

[51] Int. Cl.$^6$ .................................. B65D 5/54; B65D 5/66
[52] U.S. Cl. ....................... 229/122.1; 229/121; 229/122; 229/232
[58] Field of Search .................................. 229/121, 122, 229/122.1, 148, 232, 244; 206/459.5, 494

[56] References Cited

U.S. PATENT DOCUMENTS

| | | | |
|---|---|---|---|
| 1,855,555 | 4/1932 | Miller | 229/121 |
| 3,245,604 | 4/1966 | Chapman | 229/148 |
| 3,300,115 | 1/1967 | Schauer | 229/121 |
| 3,884,350 | 5/1975 | Johansson | 206/44.12 |
| 4,283,000 | 8/1981 | White | 229/121 |
| 4,602,735 | 7/1986 | Aaron . | |
| 5,284,293 | 2/1994 | Alpern et al. | 229/122.1 |
| 5,325,987 | 7/1994 | Alpern et al. | 220/409 |
| 5,425,474 | 6/1995 | Dalea et al. | 221/305 |
| 5,542,539 | 8/1996 | Early | 206/499 |
| 5,622,309 | 4/1997 | Matsuda et al. | 229/244 |

FOREIGN PATENT DOCUMENTS

| | | | |
|---|---|---|---|
| 462947 | 12/1991 | European Pat. Off. | 229/122 |
| 403617 | 6/1966 | Switzerland | 229/121 |
| 476449 | 12/1937 | United Kingdom | 229/244 |

Primary Examiner—Gary E. Elkins
Attorney, Agent, or Firm—Louis J. Capezzuto

[57] ABSTRACT

A dispenser carton for holding and dispensing a plurality of medical items such as surgical instruments or surgical components has a top panel, a bottom panel, and a pair of opposed side panels connected between the top panel and the bottom panel. A front panel is detachably connected to at least one of the top panel, the bottom panel, or the opposed side panels such that the front panel is movable between an open position and a closed position and defines a first dispensing location. The carton also includes a rear panel located opposite the front panel which has at least one section of the rear panel that is detachably connected to at least one of the top panel, the bottom panel or the opposed side panels. The section of the rear panel is movable between an open position and a closed position and defines a second dispensing location. This location is opposite the first dispensing location at the front panel and permits the hospital user to access and retrieve medical items from the carton at the user's option.

8 Claims, 5 Drawing Sheets

DUAL ORIENTATION DISPENSER CARTON

FIELD AND BACKGROUND OF THE INVENTION

The present invention relates, in general, to containers and, in particular, to a new and useful dispenser carton for medical items such as surgical instruments or components which can be dispensed from opposite locations of the carton.

It is a well established practice in the medical field to stock inventory of medical devices such as surgical instruments in hospitals, clinics or distributors. Normally, the medical device inventory is maintained on-site in bulk at both the hospital distributor and the hospital itself. This storage practice ensures that a ready-supply of stock is on-hand in order to meet immediate demands as they arise.

Traditionally, these medical devices, key instrument components, etc., are contained in a single package or carton. Each carton identifies the type of medical item contained therein, and normally, depending on the size of the item, multiple units of the same item are contained within the same carton.

It is not uncommon to stack numerous cartons together on the same shelf or within the same storage space. Accordingly, especially for hospital usage, it is necessary for these cartons to be easily stocked and stored within the storage space.

It is also a requirement in medical device packaging that the medical items contained within these cartons be readily accessible and retrievable. Accordingly, it is essential that the opening of the carton facilitate easy access and retrieval of the items contained therein. Additionally, it is absolutely critical that the types of product contained within the cartons be clearly differentiated by indicia, text and markings located on the exterior of the cartons, especially near the openings.

Thus, two main requirements for medical product storage for hospital usage are that the medical cartons provide a simple way to dispense the medical items and that the carton configuration alleviate unnecessary stacking and handling.

Typically, the known dispenser cartons that are commonly used in the medical industry are only capable of dispensing items or product through a single dispensing orientation after placement on the storage shelf. Since these dispenser cartons permit only one method for removing the items from the carton, the end user is limited in its stacking and handling options. One of the known types of dispenser cartons is disclosed in U.S. Pat. No. 5,325,987 (Alpern et al.) which shows a sterile package containing surgical devices in which the devices are accessible and retrievable through the top of the carton by removing the top flap.

Another known type of dispensing carton is shown in U.S. Pat. No. 4,602,735 (Aaron) which discloses a dispensing carton having a single bin-type pull-out section at the front side of the carton. Items contained within this package are retrieved at the front panel only. Accordingly, it is critical for those hospitals using this type of packaging to ensure that these cartons are stored and/or stacked in an arrangement in which the front pull-out panel is located closest to the user. Thus, the stacking orientation for this type of carton is absolutely critical since any mistake made in stacking or arranging of the carton will make it difficult to retrieve the contained items.

Presently, there is no known dispenser carton or method for dispensing medical items which meet the many different customer requirements for the storage and retrieval of products contained within these cartons.

SUMMARY OF THE INVENTION

The present invention is a dispenser carton for medical items such as surgical instruments and/or components which solves the problem normally associated with the prior art dispensing cartons. The present invention provides a dispenser carton for holding and dispensing medical items in which there are a plurality of dispensing locations on the carton which permit varying dispensing orientations as well as permit various product stacking configurations and arrangements. Accordingly, the present invention meets the hospital customer requirements for storing and dispensing product in a variety of configurations and, therefore, provides the hospital with great flexibility.

The present invention is a container or dispenser carton for holding and dispensing a plurality of medical items such as surgical instruments, surgical components or the like. The carton has a top panel, a bottom panel, and a pair of opposed side panels connected between the top panel and the bottom panel. A front panel is detachably connected to at least one of the top panel, the bottom panel, or the opposed side panels such that the front panel is movable between an open position and a closed position and defines a first dispensing location.

The carton also includes a rear panel located opposite the front panel which has at least one section of the rear panel that is detachably connected to at least one of the top panel, the bottom panel or the opposed side panels. The section of the rear panel is movable between an open position and a closed position and defines a second dispensing location. In the preferred embodiment of the invention, this location is opposite the first dispensing location at the front panel and permits the hospital user to access and retrieve medical items from the carton at the user's option.

In the preferred embodiment of this invention, the dispenser carton according to the present invention contains a plurality of medical items, such as surgical components, in a stacked configuration, for instance the items are arranged in either a horizontal or vertical stacked orientation. The items contained within the dispenser carton can be dispensed from the container at the first dispensing location from either a substantially horizontal or a substantially vertical stacked configuration. The dispensing at the second dispensing location, e.g. at the rear panel, permits the medical items to be dispensed from the container at an opposite stacked configuration from the stacked configuration of the items at the first dispensing location. Thus, if the items at the first dispensing location can be retrieved from a horizontally-stacked orientation, then the items at the second dispensing location can be retrieved from a vertically-stacked orientation. Thus, this alternative dispensing orientation of the product contained within the carton provides the user with great flexibility.

It is the object of the present invention to provide a dispenser carton for medical items which is easy to use, simple to manufacture and is cost effective.

It is another object of the present invention to provide a dispenser carton for medical items which provides a user with a variety of stacking, storing and dispensing options.

It is another object of the present invention to provide a dispenser carton for medical items which allows the user to access and retrieve these items at more than one dispensing location on the carton.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
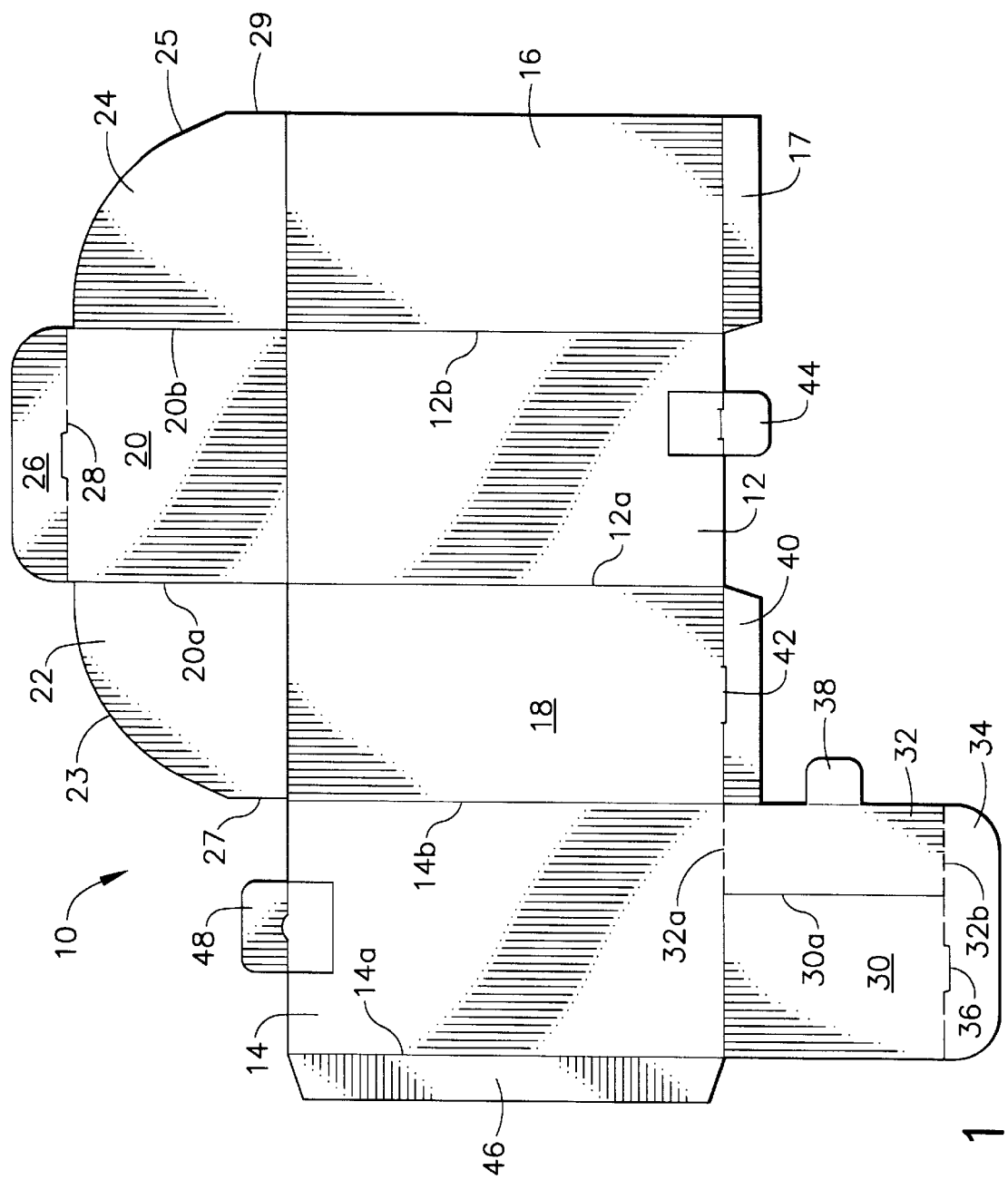
FIG. 1 is an unfolded plan view of a preferred embodiment of a dual orientation dispensing carton.

As best illustrated in FIG. 1, the present invention is a dual orientation dispenser carton for medical items such as surgical instruments and/or surgical components. The present invention is a carton, generally designated 10, comprising a bottom major panel 12 and a top major panel 14 positioned opposite the bottom major panel 12. A top minor panel 16 is connected to the bottom major panel 12 at fold line 12b and a bottom minor panel 18 is connected to the bottom major panel 12 at fold line 12a. Additionally, the bottom minor panel 18 is connected to the top major panel 14 at fold line 14b. A glue flap 46 is located adjacent fold line 14a of the top major panel 14 and is fixed to the top minor panel 16 by adhesive, glue or any other suitable securing means during the assembly of the dispenser carton 10. The top major panel 14 also includes a friction fit tab 48 which extends from the top major panel 14.

The carton 10 further comprises a horizontal end panel 20 adjacent the bottom major panel 12 having side guide panels 22 and 24 which are folded at fold lines 20a and 20b of the horizontal end panel 20. The horizontal end panel 20 also includes an insertion flap 26 having a locking slit 28 which is removably engagable with the friction fit tab 48 of the top major panel 14.

A vertical end panel 30 is located adjacent the top major panel 14 and includes an outer dispensing flap 32 having a locking tab 38. A closure lip 34 having a closure slit 36 extends along one end of the vertical end panel 30. The outer dispensing flap 32 includes perforations 32a and 32b up to a fold line 30a of the vertical end panel 30 for permitting the outer dispensing flap 32 to be partially lifted and extended away from the vertical end panel 30 by tearing along perforation lines 32a and 32b.

The bottom minor panel 18 includes an inner flap 40 having a locking slit 42 therein for receiving the locking tab 38 of the outer dispensing flap 32 in a friction-fit fashion. Accordingly, upon tearing along perforations 32a and 32b, the outer dispensing flap 32 is removably engagable with the bottom minor panel 18 at the inner flap 40.

The bottom major panel 12 also includes a closure tab 44 which is removably engagable with the closure slit 36 of the closure lip 34 of the vertical end panel 30. Additionally, the top minor panel 16 includes a closure flap 17 which is folded upon assembly to lie behind vertical end panel 30.

Figure 2:
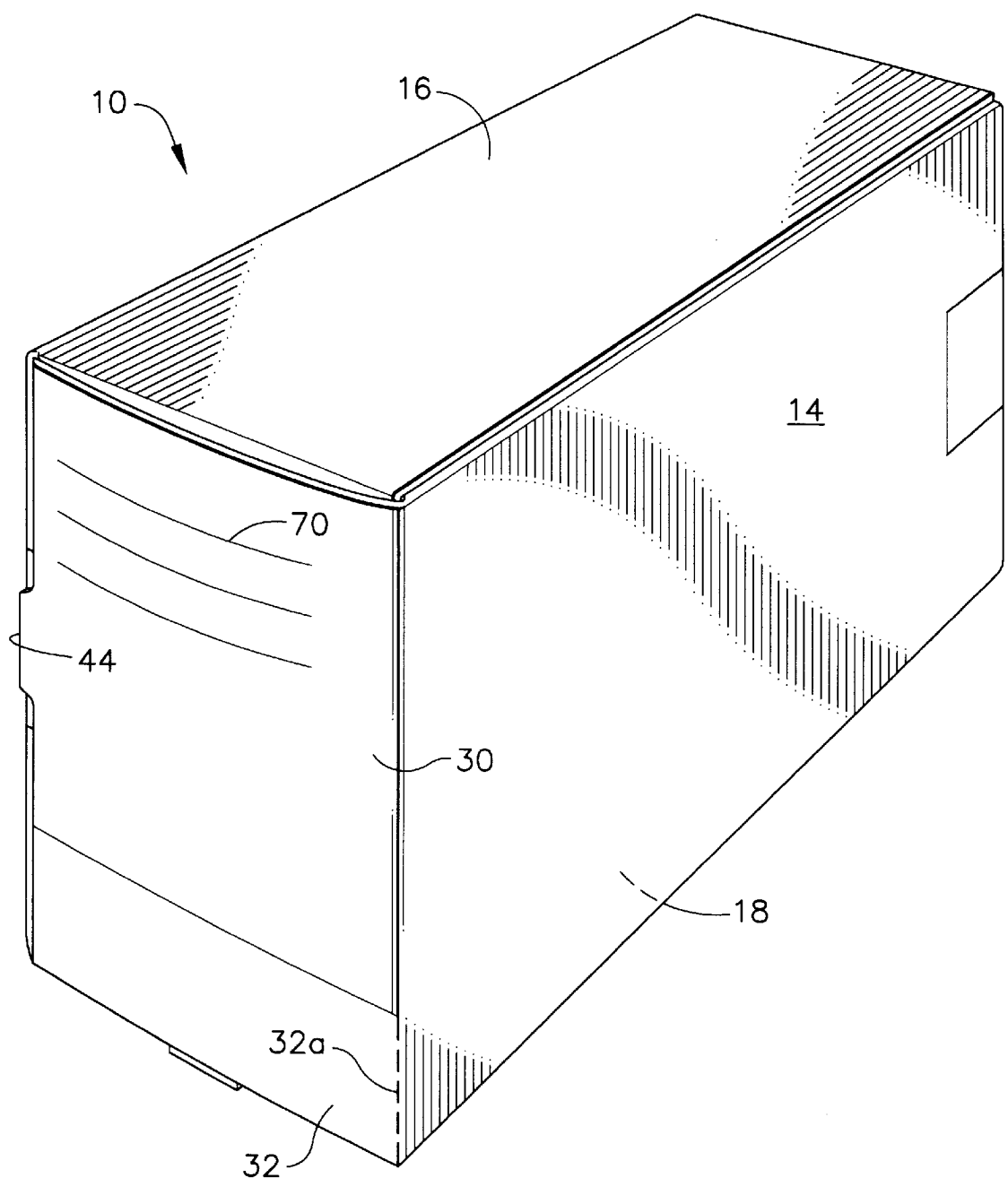
FIG. 2 is a perspective view of the assembled dual orientation dispensing carton in a vertical disposition with dispensing flaps closed.
Figure 3:
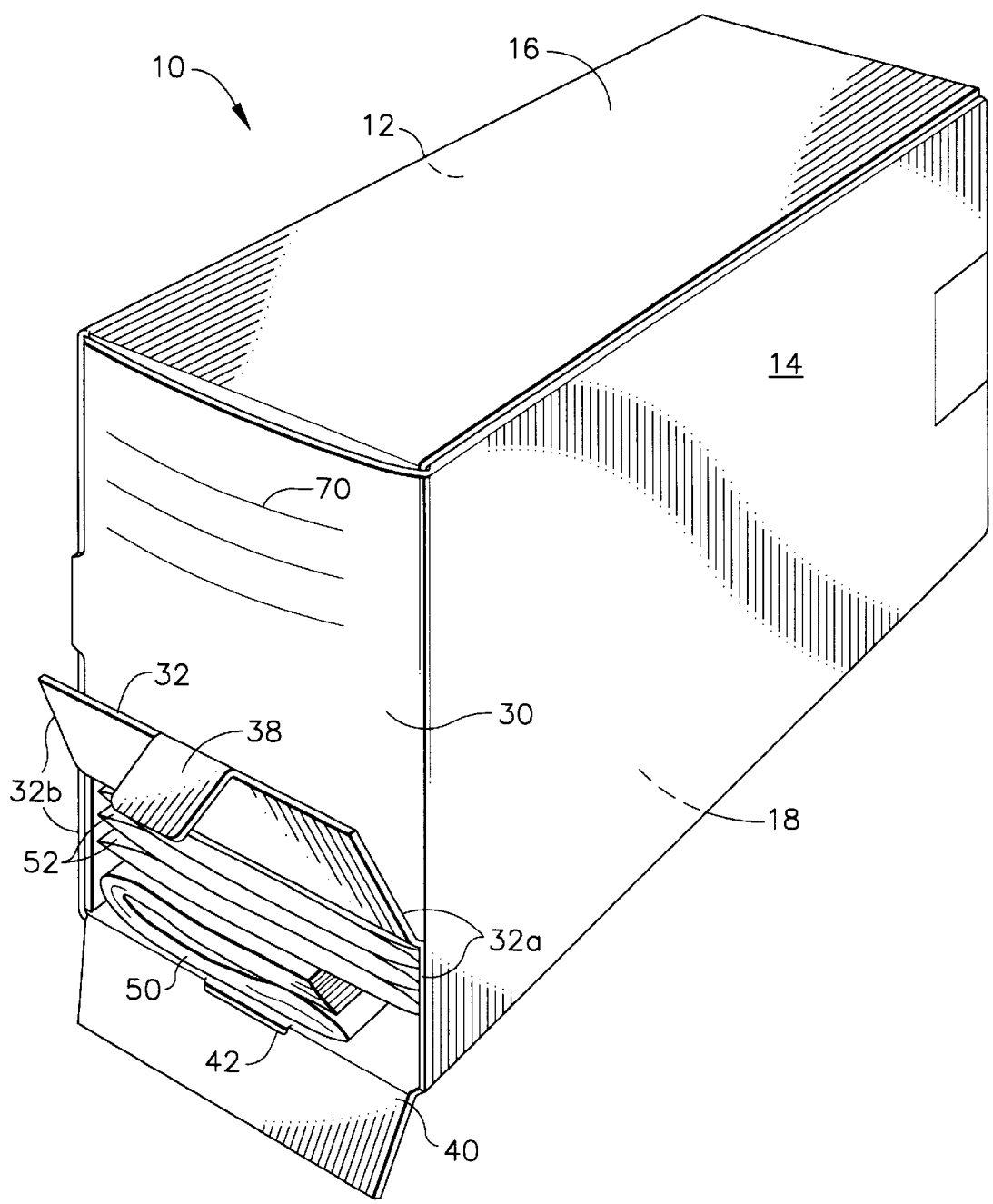
FIG. 3 is a perspective view of the assembled dual orientation dispensing carton in a vertical disposition with dispensing flaps open and product and product literature contained therein.

Upon assembly of the carton 10, as best illustrated in FIGS. 2 and 3, the vertical end panel 30 includes indicia 70 which can be text, graphics or other suitable markings on the exterior surface of the vertical end panel 30 for identifying the type of product contained within the dispenser carton 10 as well as the origin of the product, warnings, instructions or the like. As shown in FIG. 3, upon the tearing along detached perforations 32a and 32b, the outer flap 32 is partially removed from the vertical end panel 30 by displacing locking tab 38 from the locking slit 42 of the inner flap 40 thereby creating a first dispensing location for a plurality of items or surgical products 52 as well as instructions 50 contained within the carton 10. With the dispenser carton 10 in vertical disposition, the medical items 52 are arranged in a substantially horizontal stacked configuration at its first dispensing location, e.g., the outer flap 32.

Figure 4:
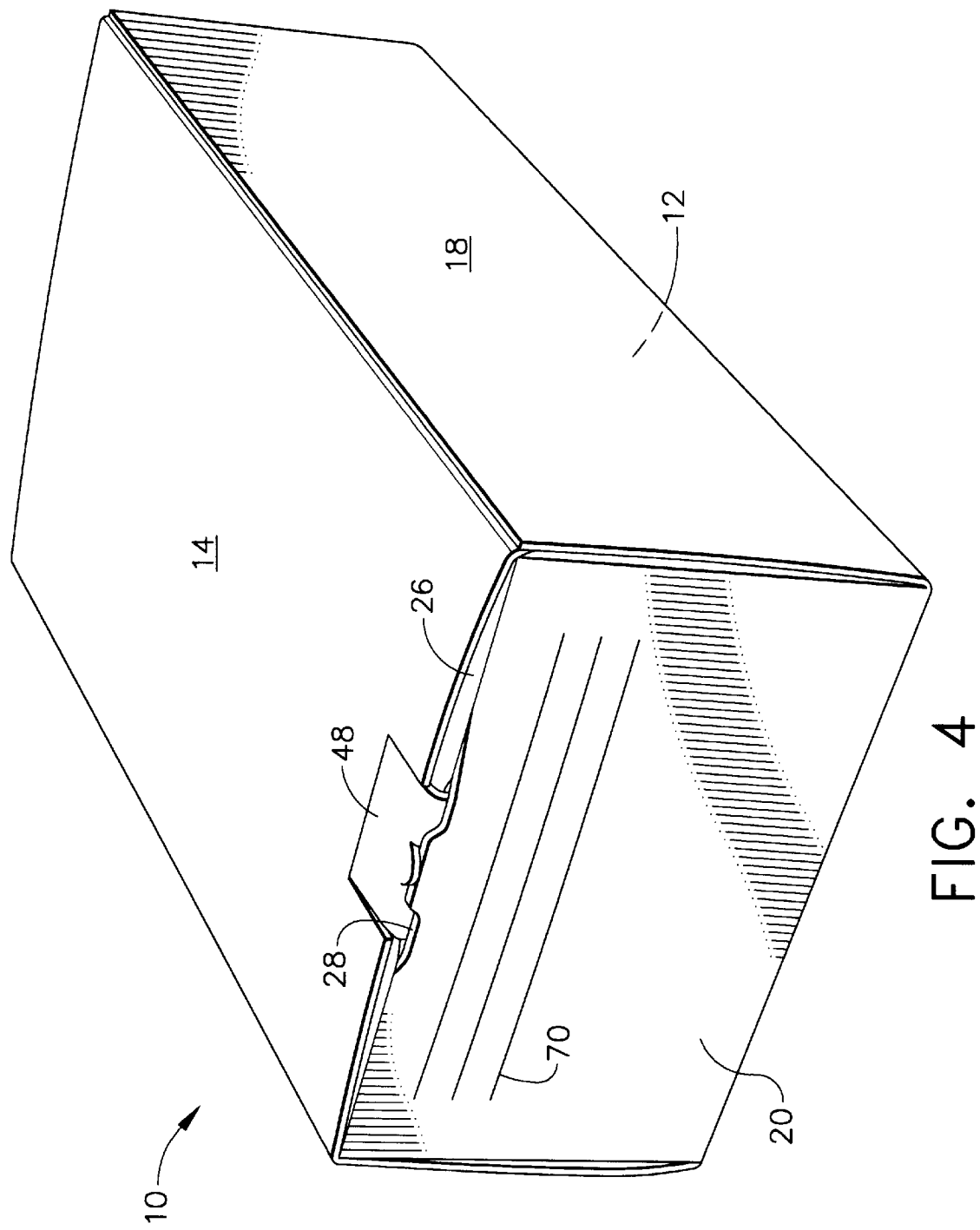
FIG. 4 is a perspective view of the assembled dual orientation dispensing carton in a horizontal disposition with dispensing flap closed.
Figure 5:
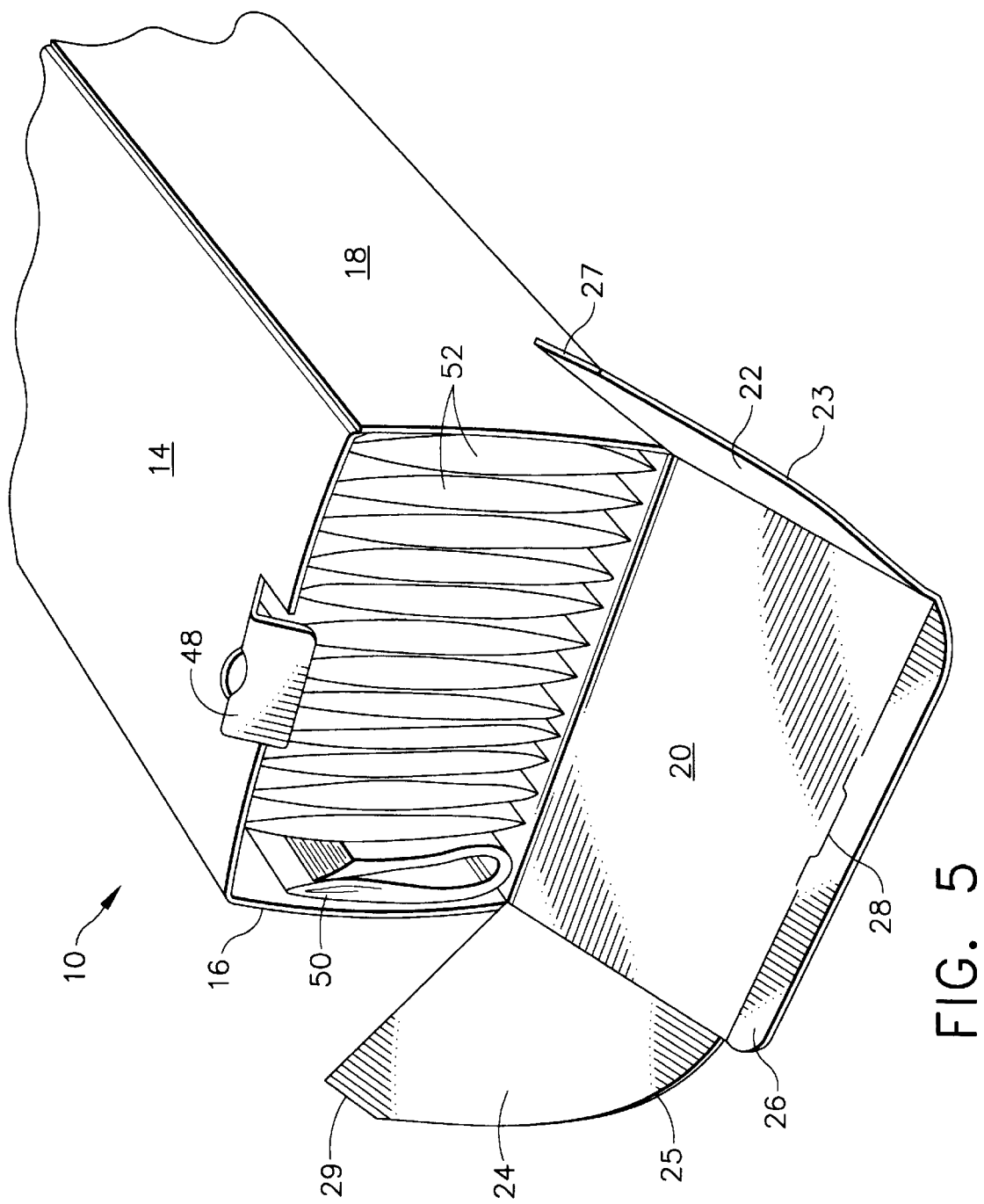
FIG. 5 is a perspective view of the assembled dual orientation dispensing carton in a horizontal disposition with dispensing flap open and removed from the carton for clarity wherein the product and literature orientation within the carton is the same as shown in FIG. 3.

Turning now to FIGS. 4 and 5, the dispenser carton 10 is in a horizontal disposition and provides a second dispensing location at the horizontal end panel 20 located opposite the vertical end panel 30 and outer flap 32 (FIGS. 2 and 3). As shown in FIG. 4, the exterior surface of the horizontal end panel 20 also includes indicia 70 for indicating the type of product 52 contained within the carton 10 as well as identifying a second dispensing location for the end user, e.g. at the horizontal end panel 20.

Upon assembly of the carton 10, the side guide panels 22 and 24 of the horizontal end panel 20 are assembled such that they are contained within the dispenser carton 10 and adjacent the top minor panel 16 and the bottom minor panel 18. The side guide panels 22 and 24 have a curved outer edge 23 and 25 respectively which facilitate the opening of the horizontal end panel 20 from the dispenser carton 10 upon disengaging the flap locking tab 48 from the locking slit 28 at the insertion lip 26. The side guide panels 22 and 24 also include stop portions 27 and 29 respectively which prevent the side guide panels 22 and 24 from being inadvertently pulled out from the container 10 upon opening of the horizontal end panel 20. The stops 27 and 29 interfere with the top panel 14 upon opening of the horizontal end panel 20 so that the horizontal end panel 20 serves as a "bin-type" opening to facilitate easy opening and closure as the user desires.

As noted above and as best illustrated in FIGS. 4 and 5, the carton 10 is in a horizontal disposition which is opposite the vertical disposition of the carton 10 shown in FIGS. 2 and 3.

Thus, the medical items 52 are stacked in a substantially vertical orientation at the second dispensing location or horizontal end panel 20. The instruction sheet 50, which may be product literature, is also readily accessible at the horizontal end panel 20 upon opening of the horizontal end panel 20.

The carton 10 permits a user to store the carton 10 in either a vertical disposition (FIGS. 2 and 3) or a horizontal disposition (FIGS. 4 and 5). This permits the user to dispense the products 52 at either the vertical end panel 30 or the horizontal end panel 20 whichever dispensing location suits the user's preference. The carton 10 also permits the user to dispense the products 52 from either a vertically stacked or horizontally stacked configuration. Accordingly, the carton 10 of the present invention provides the end user with great flexibility in both the stacking orientation and dispensing orientation.

Although this invention has been described in connection with its most preferred embodiment, it will become readily apparent to those reviewing this detailed specification that numerous additional embodiments fall well within the scope and spirit of the claimed invention as set forth in the claims which appear below.

What is claimed:

1. A container for holding and dispensing a plurality of medical items comprising:

a top panel;

a bottom panel;

a pair of opposed side panels connected between the top panel and the bottom panel;

a front panel detachably connected to at least one of the top panel, the bottom panel, or the opposed side panels; the front panel movable between an open position and a closed position for defining a first dispensing location, said front panel including a pair of curved side panels, said front panel serving as a bin-type opening;

a rear panel opposite the front panel and having at least one section which is detachably connected to at least one of the top panel, the bottom panel or the opposed side panels, the at least one section of the rear panel movable between an open position and a closed position for defining a second dispensing location, said at least one section of the rear panel having at least one perforation line for permitting said at least one section of the rear panel to be partially lifted and extended away from said rear panel by tearing along said at least one perforation line; and a plurality of medical items contained within said panels.

2. The container according to claim 1, wherein the front panel includes a front panel tab for detachably connecting the front panel to at least one of the top panel, the bottom panel or the opposed side panels.

3. The container according to claim 2, wherein the rear panel includes a rear panel tab for detachably connecting the at least one section of the rear panel to at least one of the top panel, the bottom panel or the opposed side panels.

4. The container according to claim 1, wherein the container holds the plurality of medical items in a stacked configuration.

5. The container according to claim 4, wherein the front panel permits the medical items to be dispensed from the container at the first dispensing location from either one of a substantially horizontal stacked configuration or a substantially vertical stacked configuration.

6. The container according to claim 5, wherein the rear panel permits the medical items to be dispensed from the container at the second dispensing location from another one of the substantially horizontal stacked configuration or the substantially vertical stacked configuration in a configuration opposite the stacked configuration at the first dispensing location.

7. The container according to claim 6, wherein the front panel includes readable indicia on an outer surface of the front panel.

8. The container according to claim 7, wherein the rear panel includes readable indicia on an outer surface of the rear panel.

* * * * *